United States Patent [19]

Nakamura et al.

[11] Patent Number: 5,051,419
[45] Date of Patent: Sep. 24, 1991

[54] PREVENTION OR ELIMINATION OF MYCOPLASMA CONTAMINATION OF ANIMAL OR PLANT CELL CULTURES

[75] Inventors: Shinichi Nakamura, Takatsuki; Yuzo Sakaguchi, Takaishi; Shigeki Kashimoto, Osaka; Shin-ichi Matsumoto, Ikoma, all of Japan

[73] Assignee: Dainippon Pharmaceutical Co., Ltd., Osaka, Japan

[21] Appl. No.: 371,974

[22] Filed: Jun. 27, 1989

[30] Foreign Application Priority Data

Jun. 29, 1988 [JP] Japan ................................ 63-162918

[51] Int. Cl.$^5$ .......................................... A61K 31/535
[52] U.S. Cl. .................................................. 514/235.2
[58] Field of Search ....................................... 514/235.2

[56] References Cited

U.S. PATENT DOCUMENTS 4,795,751  1/1989  Matsumoto et al. ................. 514/254

FOREIGN PATENT DOCUMENTS 0221463   5/1987   European Pat. Off. ............ 514/254
60-184014 9/1985   Japan .
62-277362 12/1987  Japan .
63-152318 6/1988   Japan .

OTHER PUBLICATIONS

Barile et al., "Mycoplasma Infection of Cell Cultures", pp. 35–45 (1978) Plenum Press, New York and London.
Egawa et al., Chem. Abstr., vol. 101, No. 25, 17 Dec. 1984, p. 757, Abstract No. 230377m.
Egawa et al., Chem. Abstr., vol. 107, No. 17, 26 Oct. 1987, p. 690, Abstract No. 154215p.
Matsumoto et al., Chem. Abstr., vol. 106, No. 1, 5 Jan. 1987, p. 268 Abstract No. 2758j.

*Primary Examiner*—Jerome D. Goldberg
*Attorney, Agent, or Firm*—Wenderoth, Lind & Ponack

[57] ABSTRACT

A method of preventing or eliminating mycoplasma contamination of animal or plant cell cultures, which comprises adding an anti-mycoplasmally effective amount of 5-amino-7-(2-aminomethylmorpholino)-1-cyclopropyl-6, 8-difluoro-1,4-dihydro-4-oxoquinoline-3-carboxylic acid or its salt to a culture medium in which animal or plant cells are cultivated; and an agent or a preparation for preventing or eliminating mycoplasma contamination of animal or plant cell cultures, comprising 5-amino-7-(2-aminomethylmorpholino)-1-cyclopropyl-6, 8-difluoro-1,4-dihydro-4-oxoquinoline-3-carboxylic acid or its salt.

6 Claims, No Drawings

PREVENTION OR ELIMINATION OF MYCOPLASMA CONTAMINATION OF ANIMAL OR PLANT CELL CULTURES

This invention relates to the prevention or elimination of contamination of animal or plant cell cultures by mycoplasma, and more specifically to the use of 5-amino-7-(2-aminomethylmorpholino)-1-cyclopropyl-6,8-difluoro-1,4-dihydro-4-oxoquinoline-3-carboxylic acid (to be referred to as "compound A" for convenience) represented by the following formula or its salt for the prevention or elimination of mycoplasma contamination of animal or plant cell cultures.

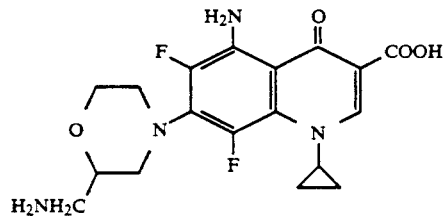

Mycoplasma stands intermediate between bacteria (class Shizomycetes) and viruses (class Microtatobiotes) in taxonomy. Mycoplasma contamination is observed in almost all cultivated animal or plant cells. The cells contaminated by mycoplasma undergo changes morphologically, genetically as well as physiologically. Mycoplasma contamination is said to reach 80 to 90% in cell cultivation on a large scale or for a long period of time. Isolated mycoplasma species are *Mycoplasma orale, Mycoplasma salivarium, Acholeplasma laidlawii, Mycoplasma arginini* and *Mycoplasma hyorhinis* [see M. F. Barile, H. E. Hopps and M. W. Grabowski in "Mycoplasma Infection of Cell Cultures", ed. G. J. McGarrity, D. G. Murphy and W. W. Nichols, p.p. 35–45 (1978), Plenum Press, New York and London].

In the production of physiologically active substances such as vaccines, hormones, antibodies and enzymes by cell cultivation, it is desired to cultivate cells while avoiding mycoplasma contamination.

Mycoplasma contamination may be considered to be prevented or eliminated by using minocycline or tiamulin which has a low minimum growth inhibitory concentration (MIC) for mycoplasma. These chemicals, however, only act bacteriostatically and not mycoplasmacidally. Hence, mycoplasma whose growth is once inhibited will again-propagate after the lapse of a certain period of time (re-contamination).

Attempts have also been made to use quinolone-type antimicrobial agents in place of minocycline or tiamulin.

EP 221463A (corresponding to U.S. Pat. No. 4,795,751) discloses that compounds of the following formula

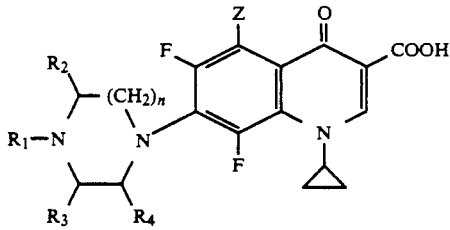

wherein Z is an amino group or a halogen atom, $R_1$ is a hydrogen atom or a methyl or ethyl group, $R_2$ is a hydrogen atom or a methyl or fluoromethyl group, $R_3$ and $R_4$ are identical or different and each represents a hydrogen atom or a methyl group, and n is 1 or 2, and esters thereof and salts thereof have anti-mycoplasma activity.

Japanese Laid-Open Patent Publication No. 152318/1988 [an abstract of which is disclosed in Central Patents Index published by Derwent Publications Ltd. under Accession No. (abbreviated as Der. No.) 88-216579/31] describes that pyridonecarboxylic acids represented by the following formula

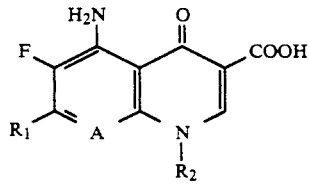

wherein $R_1$ represents a 1-piperazinyl or 1-pyrrolidinyl group which may be substituted by 1 or 2 substituents which represent an amino group, a fluorine atom or an alkyl group having 1 to 5 carbon atoms that may be substituted by a fluorine atom, an amino group, or a lower alkylamino group having 1 to 5 carbon atoms; $R_2$ represents a cyclopropyl group, or a phenyl group which may be substituted by 1 or 2 halogen atoms; A represents N, C—H or C—Y in which Y represents a halogen atom; and X represents a hydrogen atom, an amino group, or a fluorine atom, are useful as agents for preventing or eliminating mycoplasma contamination.

Attempts have also been made to eliminate mycoplasma contamination of cell cultures by using ciprofloxacin, i.e. a pyridonecarboxylic acid, either singly or in combination with tiamulin or minocycline (EP 221493A).

Japanese Laid-Open Patent Publication No. 184014/1985 (Der. No. 85-272740/44) discloses ofloxacin as an antimycoplasma agent.

However, as Test Examples to be given later on show, such a pyridonecarboxylic acid is used in high concentrations, and the ratio of its cytotoxicity to its anti-mycoplasmal activity, i.e. the safety index, is low. Accordingly, as an agent for preventing or eliminating mycoplasma contamination, it is inferior to compound A or its salts of this invention.

It has now been found in accordance with this invention that 5-amino-7-(2-aminomethylmorpholino)-1-cyclopropyl-6,8-difluoro-1,4-dihydro-4-oxoquinoline-3-carboxylic acid, i.e. compound A, and its salt have outstandingly superior anti-mycoplasma activity with low cytotoxicity, and are useful for the prevention or elimination of mycoplasma contamination of cultivated animal or plant cells.

Compound A used in this invention for preventing or eliminating mycoplasma contamination of animal or plant cell cultures is a known compound (see Japanese Laid-Open Patent Publication No. 277362/1987). However, none of the prior publications disclose that compound A has anti-mycoplasma activity.

For the purpose of this invention, compound A may be used as such, or as its salt, particularly its water-soluble salt. The salt of compound A may be a salt with an inorganic acid such as hydrochloric acid or phosphoric acid, a salt with an organic acid such as acetic acid, lactic acid, oxalic acid, succinic acid, methanesulfonic acid, maleic acid, malonic acid or gluconic acid, a salt with an acidic amino acid such as aspartic acid or glutamic acid, a salt with a metal such as sodium, potassium, calcium or magnesium, a salt with a basic amino acid such as lysine or arginine, or a salt with an organic base such as triethylamine. Preferred salts of compound A are the hydrochloride and sodium salt.

The following Test Examples demonstrate that compound A has excellent anti-mycoplasma activity with very low cytotoxicity, and are useful for the prevention or elimination of mycoplasma contamination of animal or plant cell cultures.

In Test Examples given below, the following compounds specifically disclosed in the references cited above were used controls.

Compound 1 (Japanese Laid-Open Patent Publication No. 152318/1988)

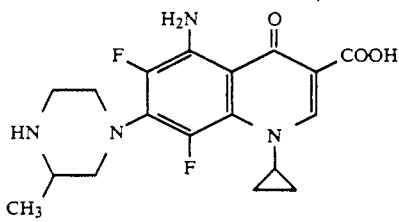

Compound 2 (EP 221493A)

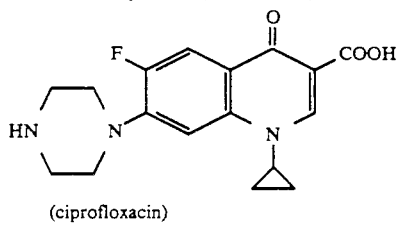

(ciprofloxacin)

Compound 3 (Merck Index 9th edition, page 806)

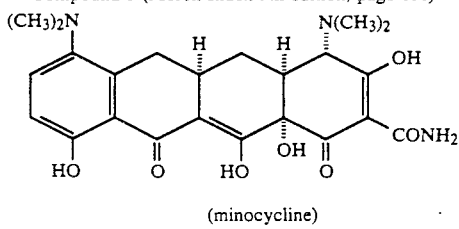

(minocycline)

Compound 4 (Japanese Laid-Open Patent Publication No. 184014/1985)

-continued (ofloxacin)

Test Example 1

Anti-mycoplasmal activity (MIC)

The minimum growth inhibitory concentrations (MIC; $\mu g/ml$) of the test chemicals were measured by the agar-dilution method.

(1) Preparation of a mycoplasma suspension for inoculation

A stored frozen suspension of mycoplasma (0.2 to 0.3 ml) was inoculated in 2 to 3 ml of a preculture medium to be described later. It was serially diluted tenfold until the dilution ratio reached 10,000 times. These diluted solutions were cultivated at 37° C. for 2 to 7 days. A culture having the highest dilution ratio was selected from those cultures in which a color change of the media was noted as a result of mycoplasma growth. It was diluted to 100 times with the preculture medium to prepare a mycoplasma suspension for inoculation.

The following preculture media were used.

For *Mycoplasma pneumoniae* and *Acholeplasma laidlawii*, Chanock liquid medium containing 0.5% glucose (pH 7.8) [Library of Bacteriology 2, "Procedures for Isolation and Identification of Human, Animal and Plant Mycoplasmas", edited by Japanese Society for Bacteriology, page 8 (1982), Saikon Publishing Co.] was used.

For *Mycoplasma hyorhinis*, a liquid medium (pH 7.8) for isolation of *Mycoplasma hyorhinis* [Journal of the Japan Veterinary Medical Association, 32, 34–38 (1979)] was used.

For other mycoplasma species, Chanock liquid medium (pH 6.8) containing 0.2% arginine was used.

(2) Preparation of agar plates containing the test chemicals

A 1,000 $\mu g/ml$ aqueous solution of each test chemical was prepared (a difficultly-soluble chemical was dissolved by adding an equimolar amount of sodium hydroxide; the same applies hereinafter). The solution was used as a base solution and its twofold serial dilutions were prepared. The diluted solutions were pipetted on plastic petri dishes each in an amount of 1 ml. The Chanock agar medium (for *Mycoplasma hyorhinis*, 0.5% mucin was further added) described at page 9 of the above cited "Procedures for Isolation and Identification of Human, Animal and Plant Mycoplasmas" was heated and kept at 55° C. and put in an amount of 9 ml in each of the petri dishes containing the test chemicals and fully mixed with the test chemicals to prepare agar plates containing the test chemicals.

(3) Measurement of MIC

The mycoplasma suspension for inoculation prepared by the procedure described in section (1) was inoculated in an amount of about 3 microliters on each of the chemical-containing agar plates by means of a Cathra-replicator (3 mm pin). The plates on which *Mycoplasma pneumoniae*, *Mycoplasma arginini*, and *Acholeplasma laidlawii* and *Mycoplasma hyorhinis* were inoculated were tightly packed in a plastic bag together with the plasic petri dishes including water-immersed absorbent cotton. *Mycoplasma pneumoniae* was aerobically cultivated at 37° C. under highly humid conditions for 7 days; and *Mycoplasma arginini* and *Acholeplasma laidlawii*, for 2 days. The other mycoplasma species were cultivated anaerobically for 2 days by using a GasPak anaerobic system (BBL). After the cultivation, growth of mycoplasma were observed under an OLYMPUS microscope (20–100 X). The lowest concentration of the test chemical at which no growth of mycoplasma was noted is defined as MIC.

The results are shown in Table 1.

TABLE 1

| Myco- | Anti-mycoplasmal activity (MIC: μg/ml) | | | | |
|---|---|---|---|---|---|
| | Compound | | | | |
| plasma* | A | 1 | 2 | 3 | 4 |
| a | 0.0125 | 0.025 | 0.39 | 0.78 | 0.78 |
| b | 0.05 | 0.2 | 1.56 | 0.1 | 1.56 |
| c | 0.1 | 0.2 | 3.13 | 0.1 | 6.25 |
| d | 0.0125 | 0.1 | 0.39 | 0.2 | 0.78 |
| e | 0.05 | 0.1 | 0.78 | 0.39 | 0.78 |
| f | 0.05 | 0.2 | 0.78 | 0.1 | 3.13 |

*The mycoplasma species used were as follows:
a: *M. pnumoniae* Mac
b: *M. orale* CH-19299
c: *M. salivarium* PG-20
d: *A. laidlawii* PG-8
e: *M. arginini* G-230
f: *M. hyorhinis* BST-7

Species a to c are isolated from humans; species d and e, from bovine; and species f, from swine. Most of these mycoplasmas are isolated frequently from contaminated cells cultivated.

As shown in Table 1, the anti-mycoplasmal activity (MIC) of compound A of this invention is more potent than those of control compounds 1 to 4. The anti-mycoplasmal activity of control compound 1 is better than those of control compounds 2 to 4, but the anti-myclo-plasmal activity of compound A is 2 to 8 times higher than that of control compound 1.

TEST EXAMPLE 2

Anti-mycoplasmal activity (MIC, MMC)

The minimum growth inhibitory concentration (MIC, μg/ml) and minimum mycoplasmacidal concentration (MMC, μg/ml) of test chemicals were measured by the liquid dilution method. The method of measuring MIC in this example differs from that used in Test Example 1.

A 1,000 μg/ml aqueous solution of a test chemical was prepared, and diluted to 5 times with a preculture medium. The dilution (200 μg/ml) was serially diluted twofold with the same medium in a 8-well reservoir. Fifty microliters of each diluted solution was distributed in the wells of a microplate. A well to which no test chemical was added was used as a control.

A mycoplasma suspension for inoculation prepared as in Test Example 1 was pipetted in an amount of 50 microliters to each of the wells. The microplates were sealed by a plate seal, shaken by a micromixer, and cultivated at 37° C. for 5 days. In the control to which no test chemical was added, color change of the medium by the growth of mycoplasma was observed after two days from the start of the cultivation. At this time, 3 microliters of the liquid culture was inoculated in drug-free Chanock agar medium by using a Cathra-replicator. The liquid culture and the agar medium were further cultivated at 37° C. for 3 days (anaerobically in the case of *M. orale*, and aerobically in the case of *A. laidlawii* and *M. arginini*). MIC and MMC were determined from the results of observation on the 5th day. MIC was defined as the lowest concentration of the test chemical at which growth of mycoplasma in the drug-containing liquid medium was not noted, and MMC, as that in the drug-free agar medium.

The results are shown in Table 2.

TABLE 2

| Test com- | Anti-mycoplasmal activity (MIC, MMC: μg/ml) | | | | | |
|---|---|---|---|---|---|---|
| | *M. orale* CH-19299 | | *A. laidlawii* PG-8 | | *M. arginini* G-230 | |
| pound | MIC | MMC | MIC | MMC | MIC | MMC |
| A | 0.05 | 0.05 | 0.0125 | 0.0125 | 0.05 | 0.05 |
| 1 | 0.39 | 0.39 | 0.2 | 0.2 | 0.1 | 0.1 |
| 2 | 1.56 | 1.56 | 0.39 | 0.39 | 0.78 | 0.78 |
| 3 | 0.39 | 25 | 0.2 | >100 | 0.39 | >100 |

As shown in Table 2, the MIC values of compounds A, 1 and 2 are identical with their MMC values. In other words, these compounds act mycoplasmacidally at the MICs.

On the other hand, compound 3 (minocycline) acts bacteriostatically, and not mycoplasmacidally, at its MIC.

The anti-mycoplasmal activity of the compound A in accordance with this invention is better than those of the control compounds.

TEST EXAMPLE 3

Activity of eliminating artificially contaminated mycoplasma

Animal cells, experimentally contaminated by mycoplasma, were cultivated for 4 days in a medium containing the test chemical and then sub-cultivated in a medium to which the test chemical was not added in order to determine whether the mycoplasma re-grew (re-contamination).

(1) Preparation of mycoplasma-contaminated cells

The mycoplasmas described in Table 3 were each pre-cultivated as in Test Example 1, (1). Two milliliters of the cultures were centifuged at $1,500 \times g$ for 30 minutes to separate the mycoplasmas. The isolated mycoplasmas were suspended in 2 ml of 10%-FBS-MEM medium (Eagle's minimum essential medium supplemented with 10% fetal bovine serum and 100 U/ml of penicillin G).

Separately, mouse fibroblast cells L-929 was suspended in 10%-FBS-MEM medium so that their density became $2.5 \times 10^4$/ml. Four milliliters of the suspension was put in a petri dish (diameter 6 cm) for tissue culture including two circular cover glasses (diameter 1.8 cm), and then 1 ml of the mycoplasma suspension described above was added. The mixture was incubated at 37° C. in 5% $CO_2$ humidified atmosphere for 3 days, and then sub-cultivated twice in order to obtain mycoplasma-contaminated cells. Mycoplasma-contamination was confirmed by the highly specific DNA-fluorochromic staining method (the above cited "Procedures for Isolation and identification of Human, Animal and Plant Mycoplasmas", pages 95–97).

(2) Experiment of eliminating mycoplasma contamination

Mycoplasma-contaminated L-929 cells were cultivated as described in the preceding section. A 1,000 μg/ml aqueous solution of a test chemical was prepared, and diluted to predetermined concentrations, with Eagle's minimum essential medium. The diluted solutions were added to the culture medium. Two petri dishes were used for each concentration of the test chemical, and two circular cover glasses were put in one of them for examination of mycoplasma. No cover glass was put in the other petri dish, and it was used for subcultivation. Cultivation in the test chemical-containing medium was carried out for 4 days, and thereafter, the cultivation was continued for 3 weeks in a drug-free medium. Medium replacement was effected every 3 to 4 days, and subcultivation was carried out once a week. Examination for mycoplasma contamination was performed on the 4th and 7th days, and thereafter every week. The mycoplasmas were detected by the highly specific DNA-fluorochromic staining method.

The results are shown in Table 3.

TABLE 3

Activity of eliminating mycoplasma contamination

| Compound | Concentration (μg/ml) | A. laidlawii PG-8 Cultivation period (days) | | | | | M. arginini G-230 Cultivation period (days) | | | | |
|---|---|---|---|---|---|---|---|---|---|---|---|
| | | 0 | 4 | 7 | 14 | 28 | 0 | 4 | 7 | 14 | 28 |
| A | 0.1 | + | − | + | + | + | + | + | + | + | + |
| | 0.2 | + | − | − | − | − | + | − | − | − | − |
| 1 | 0.2 | + | + | + | + | + | + | + | + | + | + |
| | 0.39 | + | − | − | − | − | + | − | − | − | − |
| 2 | 3.13 | + | − | − | − | − | + | + | + | + | + |
| 3 | 12.5 | + | − | + | + | + | + | − | − | + | + |

+: mycoplasma positive
−: mycoplasma negative

As shown in Table 3, for the two mycoplasma species, compound A in accordance with this invention in a concentration of 0.2 microgram/ml gave a mycoplasma negative in 4 days from the start of cultivation, and when thereafter subcultivation was performed in the absence of the compound A, no re-growth of mycoplasmas were noted. In contrast, control compound 1 also showed the activity of eliminating mycoplasma contamination, but its effective concentration was 0.39 μg/ml, which is twice that of compound A. In a system to which control compound 2 (ciprofloxacin) was added in a concentration of 3.13 micrograms/ml, the cells became mycoplasma-negative after 4 days of cultivation for *A. laidlawii* PG-8 alone. In a system to which control compound 3 (minocycline) was added in a concentration of 12.5 μg/ml, the cells were mycoplasma-negative after 4 days of cultivation, but when the chemical was removed thereafter, re-growth of mycoplasma was observed.

TEST EXAMPLE 4

Activity of eliminating spontaneously contaminated mycoplasmas

The activity of test compound to eliminate mycoplasma contamination was tested as in Test Example 3 on spontaneously contaminated human lung carcinoma cells [I] and human melanoma cells [II]. The results are shown in Table 4.

The period during which the cultivation was continued in the presence of the test chemicals was 7 days, and the mycoplasma species which infected the cells were unknown.

TABLE 4

Activity of eliminating mycoplasma contamination

| Compound | Concentration (μg/ml) | Cell [I] Cultivation period (days) | | | | Cell [II] Cultivation period (days) | | | | |
|---|---|---|---|---|---|---|---|---|---|---|
| | | 0 | 7 | 14 | 28 | 0 | 7 | 14 | 21 | 28 |
| A | 0.1 | + | + | + | + | + | − | + | + | + |
| | 0.2 | + | − | − | − | + | − | − | − | − |
| 1 | 0.2 | + | + | + | + | + | − | + | + | + |
| | 0.39 | + | − | − | − | + | − | − | − | − |
| 2 | 3.13 | + | − | + | + | + | + | + | + | + |
| | 6.25 | + | − | − | − | + | − | − | − | − |

+: mycoplasma positive
−: mycoplasma negative

The mycoplasma elminating concentration of compound A of this invention is 0.2 μg/ml which is ½ of that of control compound 1 and 1/32 of that of control compound 2 (ciprofloxacin).

TEST EXAMPLE 5

Influence on culture cells

Whether test chemicals would inhibit growth of cells was examined.

A 1,000 μg/ml aqueous solution of each of the test chemicals was serially diluted twofold with Eagle's minimum essential medium.

FL human-amnion cells ($2 \times 10^4$ cells) were suspended in 3.6 ml of 10% FBS-MEM medium, put in petri dishes (diameter 60 mm) for tissue culture, and cultivated at 37° C. in 5% $CO_2$ humidified atmosphere for 48 hours. The test chemical solution prepared as above was added in an amount of 0.4 ml to each of the petri dishes in predetermined concentrations, and the cells were cultivated for 3 days. After the cultivation, the medium was removed, and the remainder was washed once with Dulbecco's phosphate buffer (pH 7.4). The cells were peeled off by adding 0.2 ml of a 2.5% trypsin-0.002% EDTA mixed solution (1:9) and properly diluted with 10% FBS-MEM medium. Then, the number of the cells was counted by an Erma hemocytometer.

The cell proliferation rate was calculated by following formula $$\text{Cell proliferation rate} = \frac{X}{Y} \times 100$$

$X$: average number of cells* proliferated in the group containing the test chemical $Y$: average number of cells* proliferated in the control group containing no test chemical

* average number of cells proliferated =
[average cell number on 5th day] −
[average cell number on second day]

The 50% cell proliferation inhibitory concentration ($IC_{50}$: μg/ml) was graphically calculated from the concentration-proliferation rate curve.

The results are shown below.

TABLE 5

| | Cytotoxicity on FL cells | |
|---|---|---|
| Compound | $IC_{50}$ (μg/m) | $IC_{50}$/MIC |
| A | 18 | 180–1440 |
| 1 | 13.2 | 66–528 |

TABLE 5-continued

| | Cytotoxicity on FL cells | |
|---|---|---|
| Compound | IC$_{50}$ (μg/m) | IC$_{50}$/MIC |
| 2 | 28 | 9-72 |

The 50% cell proliferation inhibitory concentrations (IC$_{50}$: μg/ml) of the test compounds are higher than MICs for mycoplasmas. The ratio of IC$_{50}$ to MIC was 180-1440 for compound A, 66-528 for control compound 1, and 9-72 for control compound 2 (ciprofloxacin), and the safety range is broadest in compound A of the invention.

Another requirement of the mycoplasma contamination preventing and eliminating agent is that it should not exert deleterious effects on chromosomes of animals or plants. In this respect, the compound A of this invention is excellent.

In cell cultivation, it has been the usual practice to add an antibiotic such as Penicillin G or Streptomycin in order to prevent contamination of the culture by bacteria. Compound A also has potent antibacterial activity and is superior to control compounds 1 to 4. The MIC value of compound A on *Staphylococcus aureus* is 0.0063 and the MIC value of compound 1 is 0.025, thus compound A has about four times as potent antibacterial activity as compound 1.

Accordingly, in a culture medium to which compound A is added, the use of an antibiotic such as penicillin G or streptomycin can be omitted.

As is clearly seen from the test results given above, compound A has excellent mycoplasmacidal activity with little toxicity on cultivated cells, and can be used advantageously for protecting animal or plant cell cultures from contamination by mycoplasmas belonging to Mycoplasmatals Order including families Mycoplasmataceae, Acholeplasmataceae and Spiroplasmataceae, and/or for removing these mycoplasmas from the contaminated cell cultures.

This can be achieved according to the invention by adding compound A or its salt to a culture medium in which animal or plant cells are cultivated. The method of this invention can be applied not only to cultivation of a relatively small quantity of cells on a laboratory scale but also to the cultivation of a large quantity of cells in an industrial plant.

Generally, the cultivation of animal or plant cells is carried out by inoculating the cells in a suitable liquid medium, replacing the medium 3 to 5 days later, carrying out sub-cultivation about 7 days later after the starting of the cultivation, and repeating these operations. The medium replacement can be effected by removing the medium by suction during cultivation in the case of adhesive cells, or by centrifuging the culture medium in the case of suspended cells.

Media suitable for the cultivation of the cells may be used. For example, there can be used Minimum Essential Medium, 199 Medium, Ham's Medium, L-15 Medium, McCoy 5A Medium, CMRL 1066 Medium, RPMI 1640 Medium, NCTC 135 Medium, William's E Medium, Waymouth's Medium and Trowell's T-8 Medium.

Prevention or elimination of mycoplasma contamination may be performed by adding compound A or its salt to the culture medium before cell cultivation or at any desired time-point during the cultivation. Compound A or its salt may be present in the medium throughout the entire period of cultivation, or during part of the period. For example, it is possible to inoculate cells in a culture medium containing compound A or its salt, cultivate the cells, and then at the time of replacing the medium, continue the cultivation by using a fresh medium not containing compound A or its salt. Generally, however, compound A or its salt is present in the cultivation system throughout the entire period of cultivation.

Whether the mycoplasma contamination has been eliminated can be determined by the highly specific DNA-fluorochromic staining method.

The final concentration of compound A or its salt in cell cultures can be varied depending upon contaminating mycoplasma species, the type of the culture medium, the degree of mycoplasma contamination, etc. Generally, it is 0.2 to 10μg/ml, preferably 0.4 to 3 μ/ml, more preferably 1 to 2 μg/ml.

Compound A or its salt may be added to the medium usually as a solution or a powder so that it will attain the desired concentration. It is desirable to prepare compound as the desired formulation. The volume of the solution to be added is not more than 2% (V/V), especially not more than 1% (V/V). Addition of a large volume of the solution results in diluting the culture medium, and adversely affects the growth of cells. Generally, the concentration of compound A or its salt in the solution to be added to cell cultures is at least 15 μg/ml, preferably at least 30 μ/ml, especially preferably 40 to 70 μ/ml. The solution can be prepared by dissolving compound A or its salt in a small amount of a dilute alkali solution or a dilute acid solution, or an organic solvent such as methanol, ethanol or dimethyl sulfoxide, and diluting the solution by adding water. The solution may further contain part of the ingredients of the culture medium, a buffer, a stabilizer, etc. The solution may be freeze-dried, and used after it is re-constituted with water or a solvent. The powder formulation may usually be compound A or its salt itself, or may be a preparation obtained by mixing it with a carrier such as a powdery ingredient of the culture medium in order to facilitate weighing.

Compound A or its salt may be included in the medium beforehand as one component of the medium for cell culture. In this case, the addition of an antibiotic such as penicillin G or streptomycin may be omitted.

The following Example and Referential Example will further illustrate the invention specifically.

EXAMPLE

Production of a reagent

Fifty milligrams of compound A was dissolved in 2.4 ml of a 0.1 N aqueous NaOH solution. Water was added to the solution to adjust the volume of the solution to 0 ml. The solution was filtered by a Millipore filter, and 5 ml portions of the filtered solution were put respectively in brown vials. One milliliter of this solution contained 50μg of compound A.

REFERENTIAL EXAMPLE

Production of compound A and its salt (1) A mixture of 1 g of 5-amino-1-cyclopropyl-6,7,8-trifluoro-1,4-dihydro-4-oxoquinoline-3-carboxylic acid, 1.15 g of 2-acetylaminomethylmorpholine, 1 g of triethylamine and 10 ml of pyridine was heated under reflux for 16 hours. The reaction mixture was concentrated to dryness under reduced pressure, and ethyl acetate was added to the residue. The resulting crystals were collected by filtration, and suspended in 20 ml of water. The suspension was extracted with chloroform, and the extract was dried and concentrated. Recrystallization of the residue from ethanol gave 720 mg of 5-amino-7-(2-acetylaminomethylmorpholino)-1-cyclopropyl-6,8-difluoro-1,4-dihydro-4-oxoquinoline-3-carboxylic acid. m.p. 228°–229° C.

(2) To 600 mg of the carboxylic acid obtained in section (1) was added 15 ml of 10% hydrochloric acid, and the mixture was heated under reflux for 90 minutes. The reaction mixture was concentrated under reduced pressure. The residue was recrystallized from water-ethanol to give 300 mg of the hydrochloride of compound A. m.p. 270°–275° C. (decomp.).

(3) Two hundred milligrams of the hydrochloride of compound A obtained in section (2) was dissolved in water. The aqueous solution was neutralized with 10% aqueous ammonia and extracted with chloroform. The extract was dried and concentrated. The residue was recrystallized from ethanol to give 120 mg of compound A. m.p. 215°–217° C.

We claim:

1. A method of preventing or eliminating mycoplasma contamination of animal or plant cell cultures, which comprises adding an anti-mycoplasmally effective amount of 5-amino-7-(2-aminomethylmorpholino)-1-cyclopropyl-6,8-difluoro-1,4-dihydro-4-oxoquinoline-3-acid ("compound A" hereafter) or its salt to a culture medium in which animal or plant cells are cultivated.

2. The method of claim 1 in which compound A or its salt is added in an amount of 0.2 to 10 μg per ml of the culture medium.

3. The method of claim 2 in which compound A or its salt is added in an amount of 0.4 to 3 μg per ml of the culture medium.

4. The method of claim 1 in which compound A or its salt is added in the form of its aqueous solution.

5. The method of claim 4 in which the concentration of compound A or its salt in the aqueous solution is at least 15 μg/ml.

6. The method of claim 5 in which the volume of the aqueous solution added is not more than 2% of the volume of the culture medium.

* * * * *